United States Patent
Gottlieb (10) Patent No.: US 9,333,059 B2
(45) Date of Patent: May 10, 2016

(54) MULTI-FUNCTION ELECTRIC BRUSH APPARATUS AND SYSTEMS USEFUL FOR CLEANING TEETH AND INTERDENTAL SPACES

(71) Applicant: STEVI LLC, Silver Spring, MD (US)

(72) Inventor: Ray M. Gottlieb, Silver Spring, MD (US)

(73) Assignee: STEVI LLC, Silver Spring, MD (US)

( * ) Notice: Subject to any disclaimer, the term of this patent is extended or adjusted under 35 U.S.C. 154(b) by 7 days.

(21) Appl. No.: 14/499,163

(22) Filed: Sep. 27, 2014

(65) Prior Publication Data

US 2015/0216640 A1 Aug. 6, 2015

Related U.S. Application Data

(60) Provisional application No. 61/935,830, filed on Feb. 4, 2014.

(51) Int. Cl.
  *A61C 17/22* (2006.01)
  *A61C 15/00* (2006.01)
  *A61C 17/26* (2006.01)
  *A61C 17/34* (2006.01)

(52) U.S. Cl.
  CPC ............... *A61C 15/00* (2013.01); *A61C 17/222* (2013.01); *A61C 17/26* (2013.01); *A61C 17/3463* (2013.01)

(58) Field of Classification Search
  CPC ...... A61C 17/222; A61C 15/00; A61C 17/26; A61C 17/3463
  See application file for complete search history.

(56) References Cited

U.S. PATENT DOCUMENTS

| 4,603,448 | A | * | 8/1986 | Middleton | ............. | A61C 17/26 |
| | | | | | | 15/22.1 |
| 5,071,348 | A | | 12/1991 | Woog | | |
| 5,145,369 | A | | 9/1992 | Lustig et al. | | |
| 5,499,420 | A | | 3/1996 | Boland | | |
| 5,535,474 | A | | 7/1996 | Salazar | | |
| 5,623,746 | A | | 4/1997 | Ichiro | | |
| 5,647,385 | A | | 7/1997 | Zebuhr | | |
| 5,732,433 | A | | 3/1998 | Göcking et al. | | |
| 5,850,655 | A | | 12/1998 | Göcking et al. | | |
| 6,106,290 | A | | 8/2000 | Weissman | | |
| 6,178,579 | B1 | | 1/2001 | Blaustein | | |
| 6,230,354 | B1 | | 5/2001 | Sproat | | |
| 6,237,178 | B1 | | 5/2001 | Krammer et al. | | |

(Continued)

FOREIGN PATENT DOCUMENTS

EP 1494610 B1 12/2007

OTHER PUBLICATIONS

International Preliminary Report on Patentability for International Application No. PCT/US2014/067193, mailed Apr. 14, 2015, 4 pages.

(Continued)

*Primary Examiner* — Shay Karls
(74) *Attorney, Agent, or Firm* — Ditthavong & Steiner, P.C.; Richard A. Castellano (57) ABSTRACT

A powered dental and interdental cleaning tool may include a body, an interdental cleaning member, and a drive member. The drive member may extend from the body at an angle to a longitudinal axis of the body. The drive member may be connected to the interdental cleaning member. A neck may extend from the body and define a drive member shaft for containing and supporting the drive member.

20 Claims, 8 Drawing Sheets

(56) References Cited

U.S. PATENT DOCUMENTS

| | | | |
|---|---|---|---|
| 6,546,586 B2 | 4/2003 | Cho | |
| 6,574,820 B1 | 6/2003 | DePuydt et al. | |
| 6,735,804 B2 | 5/2004 | Carlucci | |
| 6,760,946 B2 | 7/2004 | DePuydt | |
| 7,150,061 B2 * | 12/2006 | Kwong | A61C 17/3436 15/22.1 |
| 7,311,108 B2 | 12/2007 | Getgey et al. | |
| 7,421,753 B2 | 9/2008 | Chan | |
| 7,448,107 B2 | 11/2008 | DePuydt | |
| 7,832,042 B2 | 11/2010 | DePuydt | |
| 7,941,886 B2 | 5/2011 | Chenvainu et al. | |
| 8,011,057 B2 | 9/2011 | Nejat | |
| 8,220,097 B2 | 7/2012 | DePuydt et al. | |
| 8,539,630 B2 | 9/2013 | Gatzemeyer | |
| 8,590,546 B2 | 11/2013 | Pruett | |
| 2001/0004781 A1 * | 6/2001 | Blaustein | A61C 17/22 15/28 |
| 2002/0059685 A1 | 5/2002 | Paffrath | |
| 2003/0182743 A1 * | 10/2003 | Gatzemeyer | A46B 13/02 15/22.1 |
| 2004/0123409 A1 * | 7/2004 | Dickie | A61C 17/349 15/22.1 |
| 2005/0102776 A1 | 5/2005 | Mathur | |
| 2005/0268409 A1 | 12/2005 | Blaustein et al. | |
| 2007/0294847 A1 | 12/2007 | Wang | |
| 2009/0029323 A1 | 1/2009 | Nejat | |

OTHER PUBLICATIONS

Notification of Transmittal of Translation of the International Preliminary Report on Patentability (Chapter I or Chapter II) along with Written Opinion of the International Searching Authority for International Application No. PCT/US2014/067193, mailed Apr. 14, 2015, 8 pages.

PCT/US2014/057928, Jan. 5, 2015, International Search Report and Written Opinion of International Searching Authority.

US 6,598,254, 07/2003, Blaustein et al. (withdrawn).

Non-Final Office Action for U.S. Appl. No. 14/552,434, mailed Nov. 2, 2015, 21 pages.

Notification of Transmittal of and International Preliminary Report on Patentability for International Application No. PCT/US2014/067193, mailed Jan. 19, 2016, 8 pages.

Notification of Transmittal of and International Preliminary Report on Patentability for International Application No. PCT/US2014/057928, mailed Jan. 19, 2016, 11 pages.

* cited by examiner

MULTI-FUNCTION ELECTRIC BRUSH APPARATUS AND SYSTEMS USEFUL FOR CLEANING TEETH AND INTERDENTAL SPACES

CROSS-REFERENCE TO RELATED APPLICATION

This application claims the benefit of priority to U.S. Provisional Patent Application No. 61/935,830, titled MULTI-FUNCTION ELECTRIC BRUSH APPARATUS AND SYSTEMS USEFUL FOR CLEANING TEETH AND INTERDENTAL SPACES, filed Feb. 4, 2014, the disclosure of which is hereby incorporated by reference herein in its entirety.

FIELD

The disclosure generally relates to oral hygiene tools. In particular, the disclosure relates to electric cleaning tools having a brush for cleaning teeth.

BACKGROUND

As is known, a toothbrush is an oral hygiene instrument that is useful for cleaning teeth and gums. Conventional toothbrushes may include one or more heads of bristles that are arranged for cleaning the oral cavity—particularly, the teeth, tongue, and gums. Toothpaste is typically an abrasive fluid, paste, or gel dentifrice, and is used with toothbrushes to enhance cleaning by mechanical action. The cleaning effectiveness of toothbrushes has also been enhanced by using different bristle textures, sizes, and forms. In the past century, conventional toothbrushes have been modified to include soft bristles to protect tooth enamel and minimize gum damage and/or irritation, and may be formed of nylon or other materials that have desirable hardness and durability.

Some conventional toothbrushes are powered by electricity. An electric toothbrush includes a brush that is driven by a motor and oscillates or rotates the brush. Electric toothbrushes have been found to be easier to use than brushes that require completely manual brushing action. Moreover, electric toothbrushes have been clinically proven to generally be more effective for cleaning teeth than unpowered toothbrushes.

Other types of conventional toothbrushes include interdental or interproximal brushes and end-tufted brushes. Interdental cleaning instruments such as interdental brushes are designed for cleaning between teeth, and between braces and teeth. An interdental cleaning instrument may have a cleaning head that has a tapered surface profile. For example, a head of an interdental cleaning instrument may have a conical shape for cleaning the narrow spaces between teeth. An interdental cleaning instrument may alternatively include a brush having bristles located about a slender rod that is suitable for sliding between teeth to clean interdental spaces.

End-tufted toothbrushes are designed for cleaning along gumlines adjacent to teeth. End-tufted toothbrushes typically include a bristle head that is shaped to form an angled cleaning surface that conforms to interdental spaces.

Dental instruments are conventionally required to perform specific dedicated cleaning functions for which they are narrowly suitable. Thus, an improved multi-functional electric toothbrush configured for easier, more effective, and more comprehensive tooth and interdental space cleaning may be beneficial.

SUMMARY

Certain embodiments of the present invention may provide solutions to the problems and needs in the art that have not yet been fully identified, appreciated, or solved by current dental cleaning technologies. For example, in some embodiments of the present invention, a powered multi-function brush advantageously enables simultaneous cleaning of flat tooth surfaces and interdental spaces. Further, the multi-function brush of some embodiments may be useful for orthodontic, pedodontal, and periodontal applications, and may enable enhanced subgingival cleaning.

In an embodiment, a powered dental and interdental cleaning apparatus includes a body having a first end and a second end. The apparatus has an interdental cleaning member, a drive member, and a neck. The drive member extends from the first end of the body at an angle to a longitudinal axis of the body. The drive member is connected to the interdental cleaning member. The neck has a first end and a second end, and the neck extends from the first end of the body at the first end of the neck. The neck is configured to define or contain a drive member shaft that contains the drive member.

In another embodiment, a brush assembly includes an outer brush forming a ring that defines a central opening. The brush assembly also includes an interdental cleaning member surrounded by the outer brush. The outer brush and the interdental cleaning member are configured and arranged to enable the interdental cleaning member to reciprocate axially through the opening.

In yet another embodiment, a powered dental and interdental cleaning apparatus includes an outer brush forming a ring that defines a central opening. The apparatus also includes an interdental cleaning member surrounded by the outer brush. The outer brush and the interdental cleaning member are configured and arranged to enable the interdental cleaning member to pulse or reciprocate axially through the opening. The apparatus further includes a drive assembly configured to rotate the outer brush and cause pulsing movement of the interdental cleaning member.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION

Some embodiments of the present invention pertain to a powered multi-function brush that enables simultaneous cleaning of flat tooth surfaces and interdental spaces. The multi-function brush may be useful for orthodontic, pedodontal, and periodontal applications, and may enable enhanced subgingival cleaning under the gumline. For example, the multi-function brush in some embodiments may include an interdental cleaning member that is configured to reach approximately 3 to 5 millimeters below the gumline, and preferably is configured for cleaning at about 5 millimeters below the gumline. The interdental cleaning member may reach further, however, as a matter of design choice.

Figure 1:
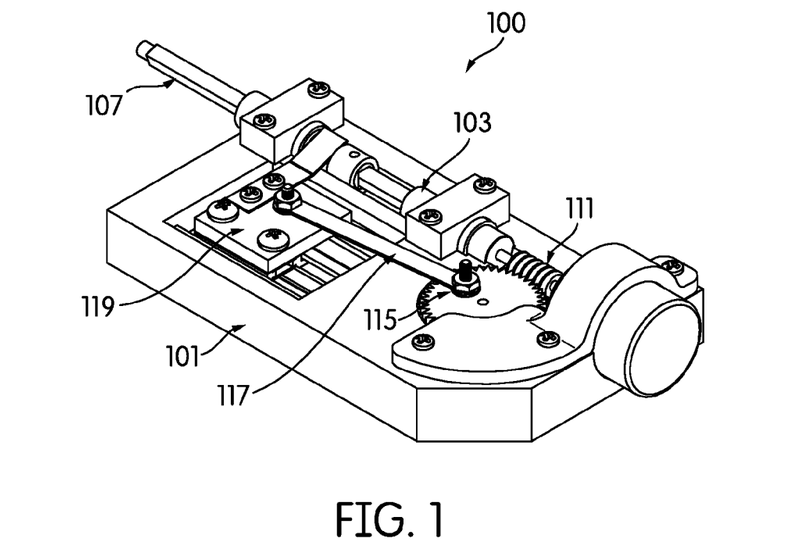
FIG. 1 is a perspective view of a drive system for a multi-functional electric brush, according to an embodiment of the present invention.

FIG. 1 is perspective view of a drive system 100 for a multi-functional electric brush, according to an embodiment of the present invention. Drive system 100 includes a body 101. Body 101 contains or supports a drive assembly 103.

Drive assembly 103 includes a drive member 107. Drive member 107 may be a shaft or any other suitable extension that would be appreciated by one of ordinary skill in the art. Drive member 107 may be connected to a brush head assembly (not shown). Drive assembly 103 includes a worm 111 that is configured to interlock with a worm gear or worm wheel 115.

Drive assembly 103 may be configured to cause rotation and pulsing of drive member 107. In particular, worm wheel 115 may be rotated, driving worm 111, which, in turn, may cause drive member 107 to rotate. Conversely, worm 111 may drive worm wheel 115. Worm wheel 115 may be configured and arranged to cause a portion of drive member 107 to reciprocate and pulse back and forth axially, in a direction perpendicular to a direction of rotation of drive member 107. For example, an arm 117 may be attached at a first end of arm 117 to worm wheel 115 at an eccentric location, as shown. A second end of arm 117 may be connected to drive member 107 and configured such that movement of arm 117 causes axial movement of drive member 107.

As shown, worm wheel 115 is attached to arm 117, which is attached to a movable portion 119 of drive system 100. Movable portion 119 may be configured to contact and move drive member 107. Movable portion 119 may be arranged on tracks that enable movement of movable portion 119 caused by worm wheel 115. Movable portion 119 is connected to drive member 107 for moving drive member 107 as a result of rotation of worm wheel 115. As such, the rotation of worm wheel 115 may cause a combination of rotation and axial movement or pulsing of drive member 107.

Figure 2:
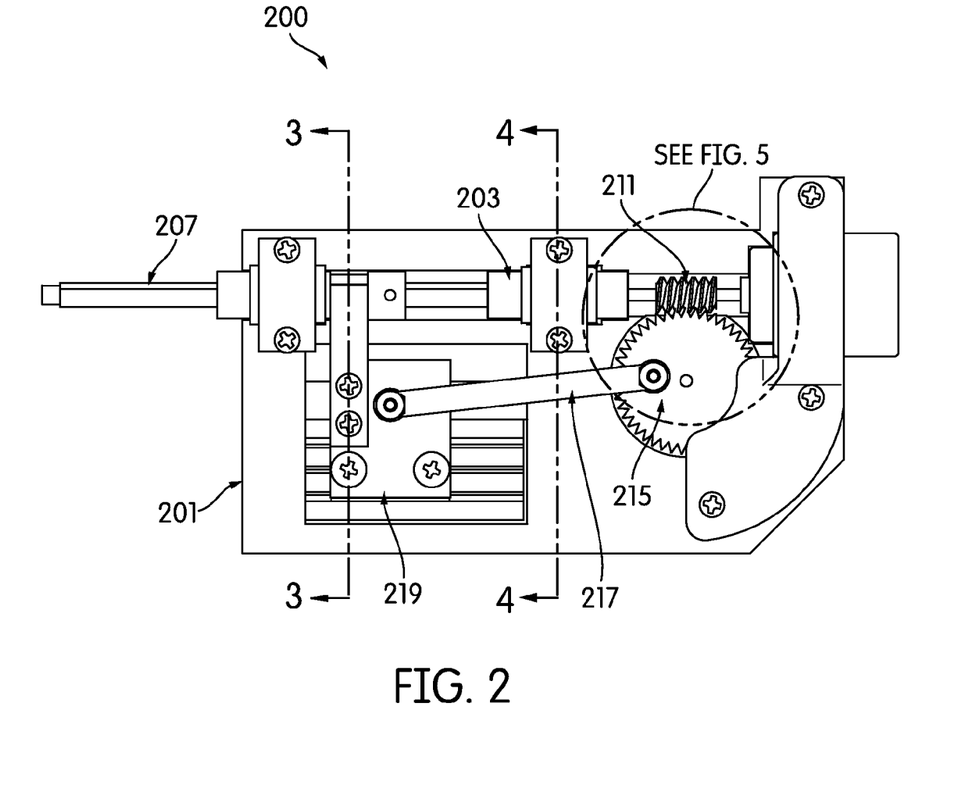
FIG. 2 is a top view of a drive system for a multi-functional electric brush, according to an embodiment of the present invention.

FIG. 2 is a top view of a drive system 200 for a multi-functional electric brush, according to an embodiment of the present invention. Drive system 200 has a body 201. Body 201 contains or supports a drive assembly 203.

Drive assembly 203 includes a drive member 207. Drive member 207 may be connected to a brush head assembly (not shown). Drive assembly 203 includes a worm 211 that is configured to interlock with a worm gear or worm wheel 215.

Drive assembly 203 may be configured to cause rotation and pulsing of drive member 207. In particular, worm wheel 215 may be caused to rotate, driving worm 211, which, in turn, may cause shaft 207 to rotate. Conversely, worm 211 may drive worm wheel 215. Worm wheel 215 may be configured and arranged to cause a portion of drive member 207 to reticulate back and forth axially, in a direction perpendicular to a direction of rotation of drive member 207. For example, an arm 217 may be attached at a first end of arm 217 to worm wheel 215 at an eccentric location, as shown. A second end of arm 217 may be connected to drive member 207 and configured such that movement of arm 217 causes axial movement of drive member 207.

As shown, worm wheel 215 is attached to arm 217, which is attached to a movable portion 219 of drive system 200. Movable portion 219 may be configured to contact and move drive member 207. Movable portion 219 may be arranged on tracks that enable movement of movable portion 219 caused by worm wheel 215. Movable portion 219 is connected to drive member 207 for moving drive member 207 as a result of rotation of worm wheel 215. As such, the rotation of worm wheel 215 may cause a combination of rotation of drive member 207 and axial movement or pulsing of drive member 207.

Figure 3:
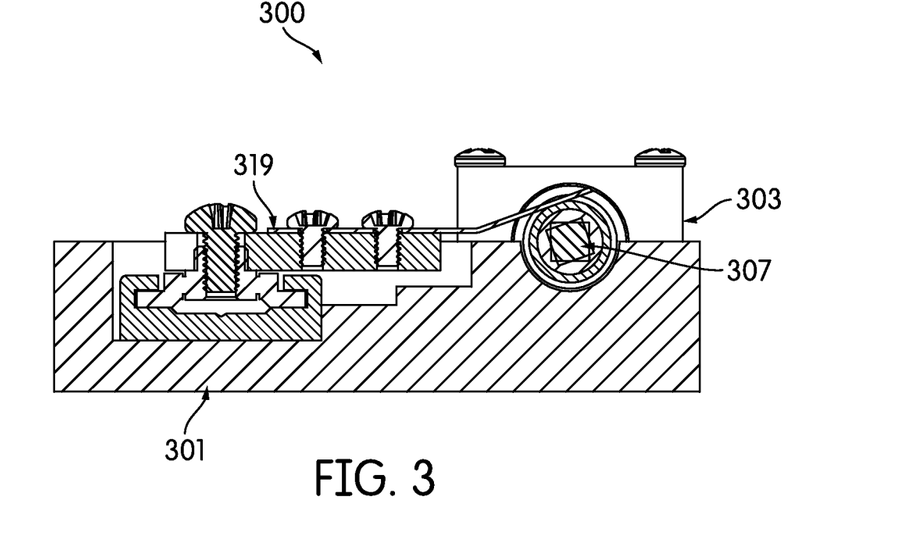
FIG. 3 is a cross-sectional view of a drive system, according to an embodiment of the present invention.

FIG. 3 is a cross-sectional view of a drive system 300, according to an embodiment of the present invention. Drive system 300 has a body 301. Body 301 contains or supports a drive assembly 303.

Drive assembly 303 includes a drive member 307. Drive member 307 may be connected to a brush head assembly (not shown). Drive system 303 may include a worm (not shown) that is configured to interlock with a worm gear or worm wheel (not shown). For example, the worm gear and the worm may be selected to be at a 4:1 ratio. Accordingly, for every four rotations of drive member 307, drive member 307 would pulse in and out in one movement. Drive system 303 may be configured to cause rotation and pulsing of drive member 307.

Figure 4:
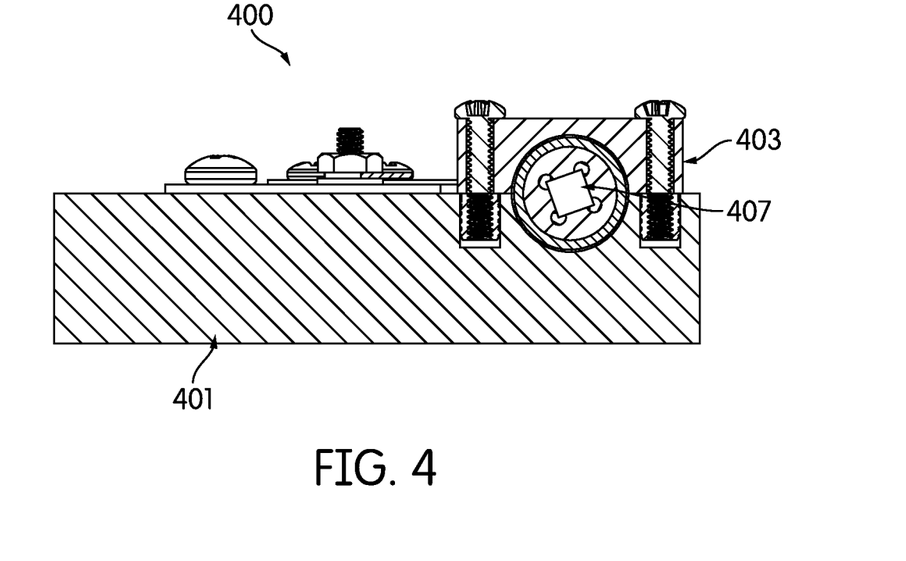
FIG. 4 is another cross-sectional view of a drive system, according to an embodiment of the present invention.

FIG. 4 is a cross-sectional view of a drive system 400, according to an embodiment of the present invention. Drive system 400 includes a body 401. Body 401 contains or supports a drive assembly 403.

Drive assembly 403 includes a drive member 407. Drive member 407 may be connected to a brush head assembly (not shown). Drive system 403 may include a worm (not shown) that is configured to interlock with a worm gear or worm wheel (not shown). Drive system 403 may be configured to cause rotation and pulsing of drive member 407.

Figure 5:
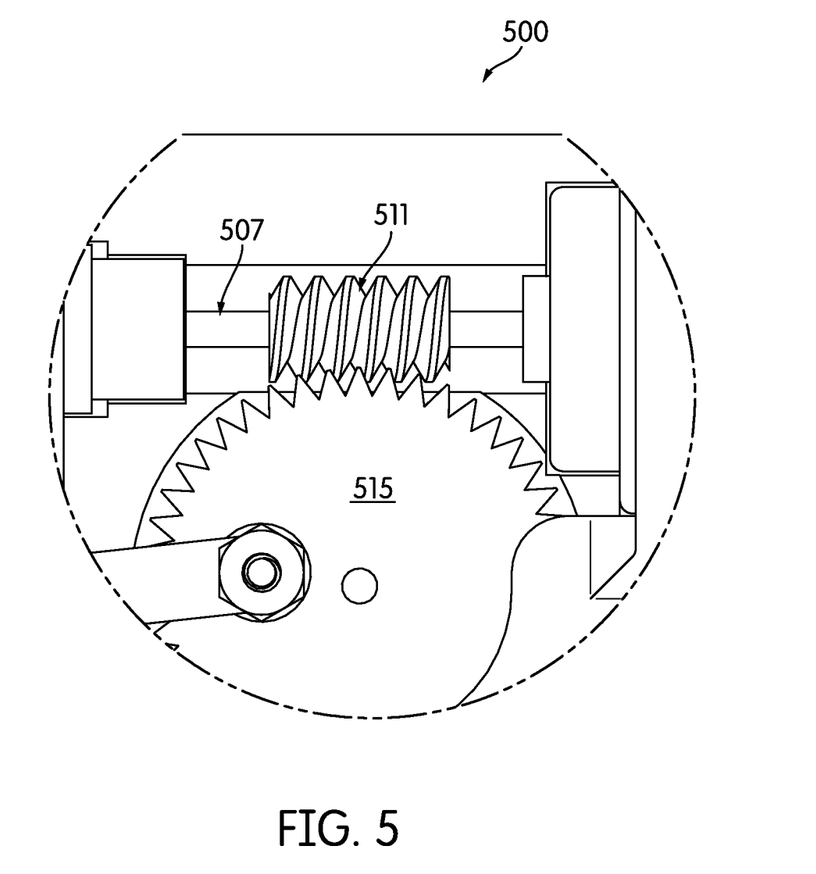
FIG. 5 is an exploded view of a drive system, according to an embodiment of the present invention.

FIG. 5 is a cross-sectional view of a drive system 500, according to an embodiment of the present invention. Drive system 500 includes a drive member 507. Drive member 507 may be connected to a brush head assembly (not shown). Drive system 500 includes a worm 511 that is configured to interlock with a worm gear or worm wheel 515. Drive system 500 may be configured to cause rotation and pulsing of drive member 507. As shown in FIG. 5, worm 511 is fixed to the drive member 507 and configured to interlock with worm wheel or worm gear 515. Worm gear 515 may be caused to move and thus rotate worm 511 to cause rotation of drive member 507. Conversely, worm 511 may be caused to rotate, and thus rotate worm gear 515.

Figure 6:
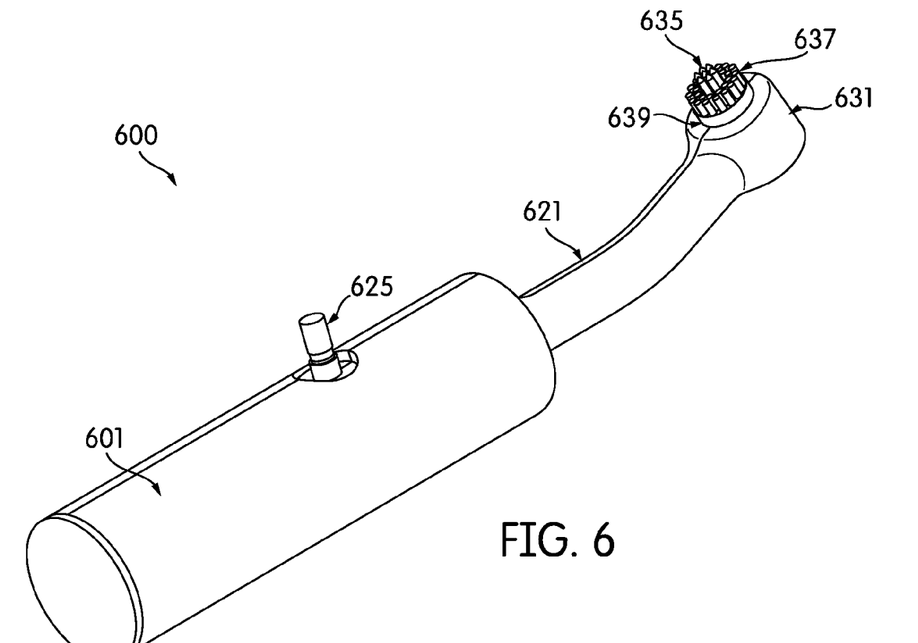
FIG. 6 is a perspective view of a multi-functional electric brush, according to an embodiment of the present invention.

FIG. 6 is a perspective view of a multi-functional electric brush 600, according to an embodiment of the present invention. Multi-functional electric brush 600 includes a body 601. Body 601 contains or supports a drive system (not shown).

Body 601 is connected to a neck 621 at a first end of neck 621. A brush assembly head 631 may extend from or be connected to a second end of neck 621. Body 601 may define an opening for access to the drive system. A button, switch, or other now known or later developed actuating mechanism 625 may be connected to the drive system and accessible through the opening of body 601. Actuating mechanism 625 may be configured to enable and cause an adjustment of the drive system. For example, actuating mechanism 625 may facilitate turning on and off the device, and adjusting a speed of the drive system of multi-functional electric brush 600. In some embodiments, the drive system may be connected to a variable speed motor (not shown). The motor and actuating mechanism 625 may be configured for variable speed adjustment of the motor, and thus variable speed adjustment of the drive system.

Drive member 607 may be flexible to accommodate angled extension from body 601 to a brush assembly 631. In some embodiments, the angle may be about 20 degrees. As shown in FIG. 6, body 601 and neck 621 may have a unitary construction where body 601, neck 621, and brush assembly 631 form a substantially unitary construction. For example, portions of body 601, neck 621, and brush assembly 631 may be formed from a single material.

The brush assembly includes interdental cleaning member 635 and an outer brush member 637. Outer brush member 637 may be configured to form a ring defining a central opening, and interdental cleaning member 635 may be disposed for movement inside the ring in a direction substantially perpendicular to a direction of rotation of brush member 637. Outer brush member 637 is supported by a brush support member 639. Multi-functional electric brush 600 is advantageously suitable for cleaning tooth surfaces, and particularly for cleaning tooth surfaces in areas of the mouth that are difficult to reach, including interdental regions and spaces.

Figure 7:
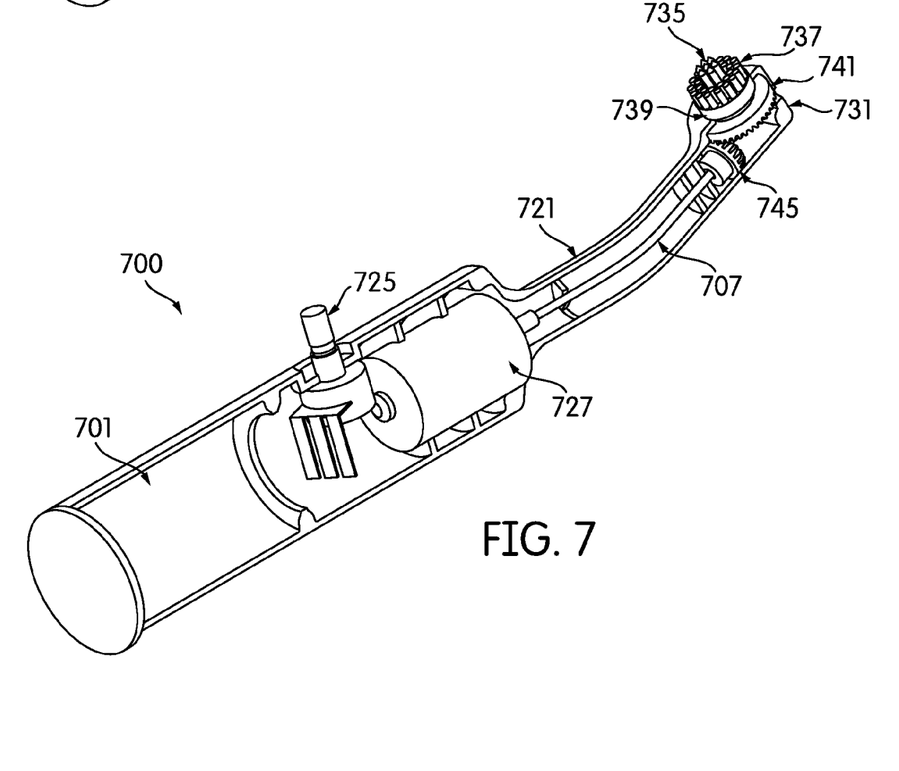
FIG. 7 is a perspective cutaway view of a multi-functional electric brush showing a drive system, according to an embodiment of the present invention.

FIG. 7 is a perspective view of a multi-functional electric brush 700, according to an embodiment of the present invention. Multi-functional electric brush 700 has a body 701. Body 701 contains or supports a drive system. The drive system shown in FIG. 7 is in accordance with a different embodiment than that shown in FIG. 1. The drive system includes a drive member 707. Drive member 707 may be a flexible shaft in some embodiments.

Body 701 is connected to a neck 721 at a first end of neck 721. Neck 721 may include support structures that support drive member 707. Drive member 707 may include a cable, wire, flexible shaft or rod, or any other suitable structure. Drive member 707 may be formed of metal, an alloy, a polymer, a composite, or any other suitable material that is now known or later developed. A head assembly 731 is connected to a second end of neck 721. A button, switch, or other now known or later developed actuating mechanism 725 is connected to the drive system and through an opening of body 701. Actuating mechanism 725 may be configured to enable and cause an adjustment of the drive system. For example, actuating mechanism 725 may facilitate turning multi-functional electric brush 700 on and off and adjusting a speed of the drive system. In some embodiments, the drive system may be connected to a variable speed motor (not shown). The motor and actuating mechanism 725 may be configured for variable speed adjustment of the motor, and thus variable speed adjustment of the drive system.

Drive member 707 is connected to a motor 727 at a first end of drive member 707. Motor 727 may be powered by a power source. The power source may be a battery power source, power from an outlet, or any other suitable AC or DC source, for example. Motor 727 may be connected to actuating mechanism 725 to enable variable speed control. Motor 727 may be anchored for rotation inside body 701.

Drive member 707 may be flexible to accommodate angled extension from body 701 to a brush assembly 731. In some embodiments, the angle may be about 20 degrees. Brush assembly 731 may include an interdental cleaning member 735 and an outer brush member 737. Outer brush member 737 may be configured to form a ring defining a central opening, and interdental cleaning member 735 may be disposed for movement inside the ring in a direction substantially perpendicular to a direction of rotation of brush member 737.

Outer brush member 737 may be supported by a brush support member 739. Drive member 707 may be contained or supported within a drive shaft defined by neck 721. Support structures formed in or defined by the interior of neck 721 may be useful for supporting an angled, flexible drive member. Drive member 707 may be connected at a second end to a crankshaft assembly having a brush assembly support gear 741 and a drive member gear 745. Drive member gear 745 may be attached to and rotated by drive member 707. Drive member gear 745 may be configured to interlock with and cause rotation of brush assembly support gear 741.

The second end of drive member 707 may be attached to an offset connecting rod (not shown). The connecting rod may be associated with a ball and socket assembly (not shown). The ball and socket assembly may connected to interdental cleaning member 735 and may be configured to cause interdental cleaning member 735 to move up and down in a direction perpendicular to the direction of rotation of drive member 707 as drive member 707 rotates.

Brush support member 739 may be connected to brush assembly gear 741. When drive member 707 is rotated by motor 727, drive member gear 745 is caused to rotate brush assembly gear 741, thus rotating outer brush 737 attached to brush support 739. Meanwhile, rotating drive member 707 moves the connecting rod to cause pulsing movement of interdental cleaning member 735 through the central opening of outer brush 737. In some embodiments, interdental cleaning member 735 may also be connected to brush assembly gear 741 to enable rotation of cleaning member 735 during the pulsing. For example, when a gear ratio of brush assembly gear 741 and drive member gear 745 is 1:2, interdental cleaning member 735 may rotate at a same speed as outer brush 737, and pulse in a direction perpendicular to a direction of rotation at a speed of about twice the speed of rotation of interdental cleaning member 735. Accordingly, multi-function brush 700 advantageously enables simultaneous cleaning of flat tooth surfaces and interdental spaces.

Figure 8:
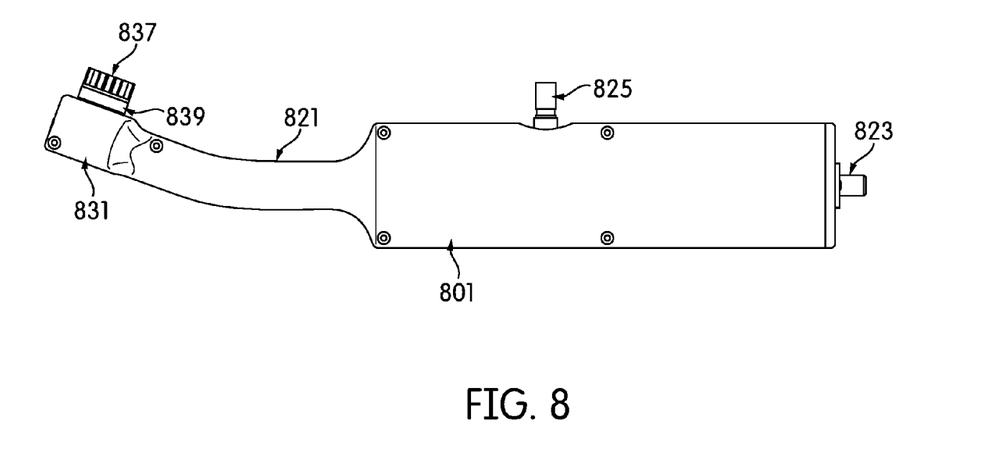
FIG. 8 is a side view of a multi-functional electric brush, according to an embodiment of the present invention.

FIG. 8 is a side view of a multi-functional electric brush 800, according to an embodiment of the present invention. Multi-functional electric brush 800 includes a body 801. Body 801 contains or supports a drive system (not shown).

Body 801 is connected to a neck 821 at a first end of neck 821. A head 831 is connected to a second end of neck 821. Body 801 may define an opening for access to the drive system. A button, switch, or other now known or later developed actuating mechanism 825 may be connected to the drive system and accessible through the opening of body 801. Actuating mechanism 825 may be configured to enable and cause an adjustment of the drive system. For example, actuating mechanism 825 may facilitate turning multi-functional electric brush 800 on and off and adjusting a speed of the drive system. In some embodiments, the drive system may be connected to a variable speed motor (not shown). The motor and actuating mechanism 825 may be configured for variable speed adjustment of the motor, and thus variable speed adjustment of the drive system.

Drive member 807 may be flexible to accommodate angled extension from body 801 to a brush assembly 831. In some embodiments, the angle may be about 20 degrees. Brush assembly 831 may include the interdental cleaning member (not shown) and an outer brush member 837. Outer brush member 837 may be configured to form a ring defining a central opening, and the interdental cleaning member may be disposed for movement inside the ring in a direction substantially perpendicular to a direction of rotation of brush member 837. Outer brush member 837 may be supported by a brush support member 839. Multi-functional electric brush 800 shown in FIG. 8 is advantageously suitable for cleaning tooth surfaces, and particularly for cleaning tooth surfaces in areas of the mouth that are difficult to reach, including interdental regions and spaces.

Figure 9:
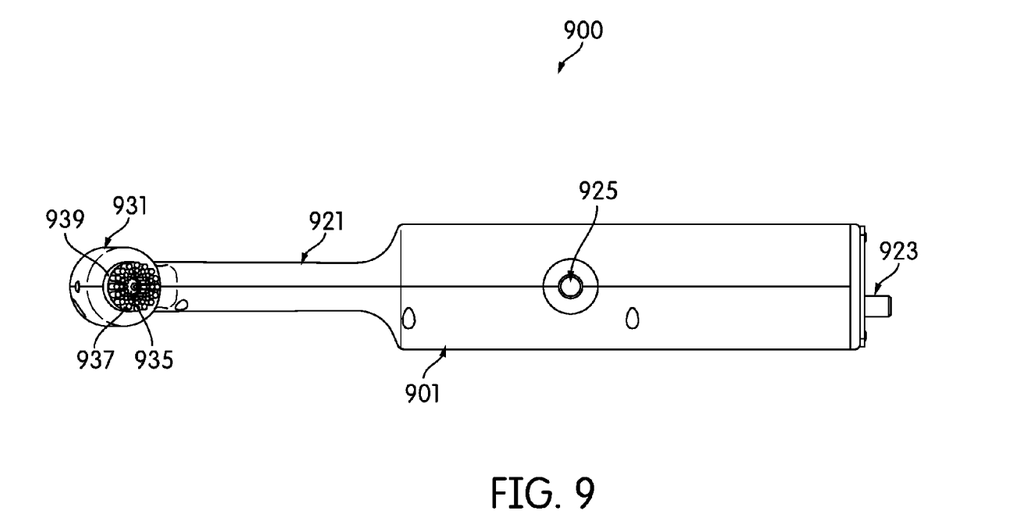
FIG. 9 is a top view of a multi-functional electric brush, according to an embodiment of the present invention.

FIG. 9 a top view of a multi-functional electric brush 900, according to an embodiment of the present invention. Multi-functional electric brush 900 includes a body 901. Body 901 contains or supports a drive system.

Body 901 is connected to a neck 921 at a first end of neck 921. A head 931 is connected to a second end of neck 921. Body 901 may define an opening for access to the drive system. A button, switch, or other now known or later developed actuating mechanism 925 may be connected to the drive system and accessible through the opening of body 901. Actuating mechanism 925 may be configured to enable and cause an adjustment of the drive system. For example, actuating mechanism 925 may facilitate turning multi-functional electric brush 900 on and off, and adjusting a speed of the drive system.

Drive member 907 may be flexible to accommodate angled extension from body 901 to a brush assembly 931. In some embodiments, the angle may be about 20 degrees. The brush assembly may include an interdental cleaning member 935 and an outer brush member 937. Outer brush member 937 may be configured to form a ring defining a central opening, and interdental cleaning member 935 may be configured and arranged for movement inside the ring in a direction substantially perpendicular to a direction of rotation of outer brush member 937. Outer brush member 937 may be supported by a brush support member 939. Multi-functional electric brush 900 is advantageously suitable for cleaning tooth surfaces, and particularly for cleaning tooth surfaces in areas of the mouth that are difficult to reach, including interdental regions and spaces.

Figure 10:
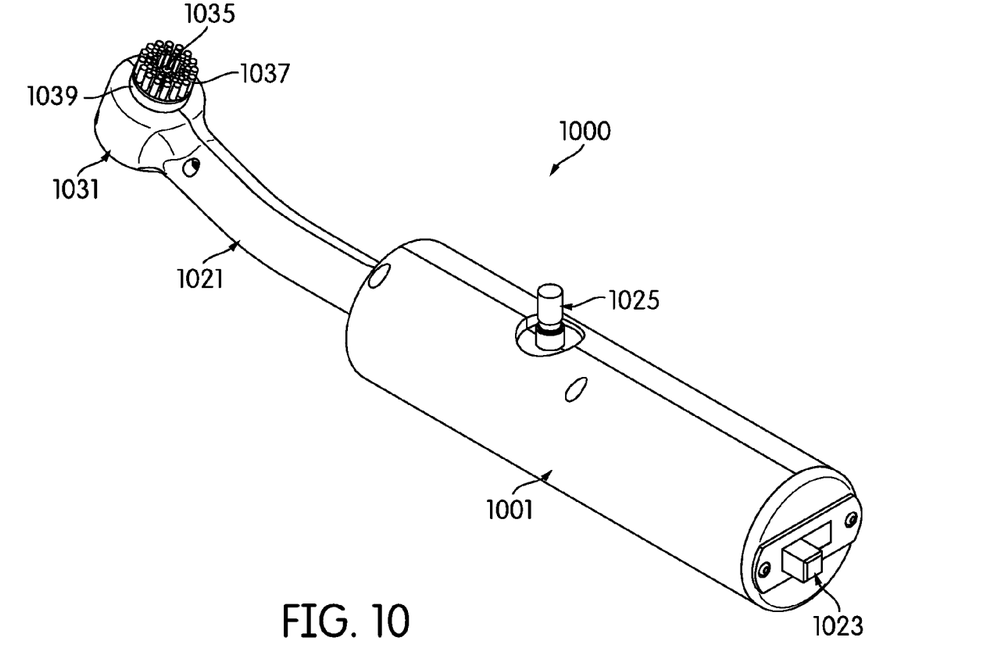
FIG. 10 is a perspective view of a multi-functional electric brush, according to an embodiment of the present invention.

FIG. 10 is a perspective view of a multi-functional electric brush 1000, according to an embodiment of the present invention. Multi-functional electric brush 1000 has a body 1001. Body 1001 contains or supports a drive system (not shown).

Body 1001 is connected to a neck 1021 at a first end of neck 1021. A head 1031 is connected to a second end of neck 1021. Body 1001 may define an opening for access to the drive system. A first button, switch, or other now known or later developed actuating mechanism 1023 may be included at an end of body 1001 as shown in FIG. 10. Switch 1023 may be configured to power a drive system of multi-functional electric brush 1000 on and off. A second button, switch, or other now known or later developed actuating mechanism 1025 may be connected to the drive system and accessible through the opening of body 1001. Actuating mechanism 1025 may be configured to enable and cause an adjustment of the drive system. For example, actuating mechanism 1025 may facilitate turning multi-functional electric brush 1000 on and off and adjusting a speed of the drive system.

Drive member 1007 may be flexible to accommodate angled extension from body 1001 to a brush assembly 1031. In some embodiments, the angle may be about 20 degrees. The brush assembly may include an interdental cleaning member 1035 and an outer brush member 1037. Outer brush member 1037 may be configured to form a ring defining a central opening, and interdental cleaning member 1035 may be disposed for movement inside the ring in a direction substantially perpendicular to a direction of rotation of outer brush member 1037. Outer brush member 1037 is supported by a brush support member 1039. Multi-functional electric brush 1000 is advantageously suitable for cleaning tooth surfaces, and particularly for cleaning tooth surfaces in areas of the mouth that are difficult to reach, including interdental regions and spaces.

Figure 11:
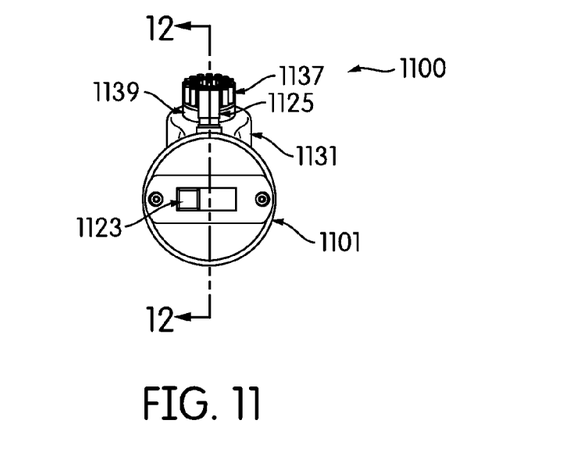
FIG. 11 is an end view of a multi-functional electric brush, according to an embodiment of the present invention.

FIG. 11 is an end view of a multi-functional electric brush 1100, according to an embodiment of the present invention. Multi-functional electric brush 1100 includes a body 1101. Body 1101 contains or supports a drive system (not shown).

Body 1101 is connected to a neck 1121 at a first end of neck 1121. A head 1131 may be connected to a second end of neck 1121. As shown in FIG. 11, body 1101 and neck 1121 may have a unitary construction where body 1101, neck 1121, and brush assembly 1131 form a substantially unitary construction. For example, portions of body 1101, neck 1121, and brush assembly 1131 may be formed from a single material.

A first button, switch, or other now known or later developed actuating mechanism 1123 may be included at an end of body 1101 as shown in FIG. 11. Switch 1123 may be configured to power a drive system of multi-functional electric brush 1100 on and off. A second button, switch, or other now known or later developed actuating mechanism 1125 may be connected to the drive system and accessible from an outer portion of body 1101.

Actuating mechanism 1125 may be configured to enable and cause an adjustment of the drive system. For example, actuating mechanism 1125 may facilitate turning multi-functional electric brush 1100 on and off and adjusting a speed of the drive system. In some embodiments, the drive system may be connected to a variable speed motor (not shown). The motor and actuating mechanism 1125 may be configured for variable speed adjustment of the motor, and thus variable speed adjustment of the drive system.

Drive member 1107 may be flexible to accommodate angled extension from body 1101 to a brush assembly 1131. In some embodiments, the angle may be about 20 degrees. The brush assembly may include an interdental cleaning member (not visible) and an outer brush member 1137. Outer brush member 1137 may be configured to form a ring defining a central opening, and the interdental cleaning member may be disposed for movement inside the ring in a direction substantially perpendicular to a direction of rotation of brush member 1137. Outer brush member 1137 may be supported by a brush support member 1139. Multi-functional electric brush 1100 is advantageously suitable for cleaning tooth surfaces, and particularly for cleaning tooth surfaces in areas of the mouth that are difficult to reach, including interdental regions and spaces.

Figure 12:
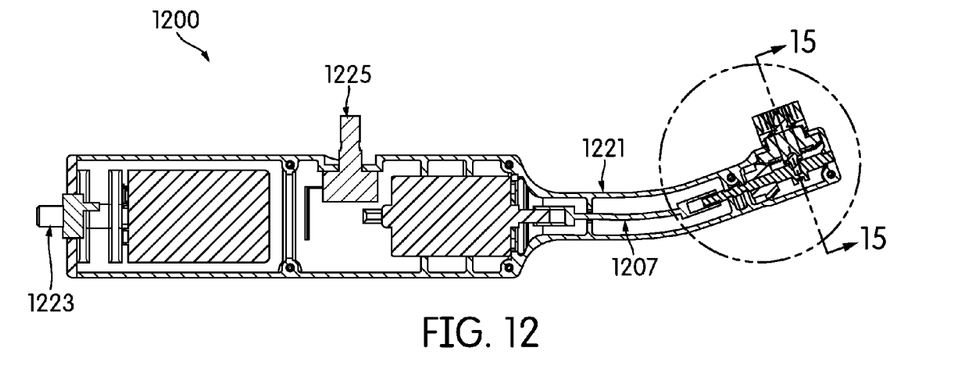
FIG. 12 is a cross-sectional view of a multi-functional electric brush, according to an embodiment of the present invention.

FIG. 12 is a side view of a multi-functional electric brush 1200, according to an embodiment of the present invention. Multi-functional electric brush 1200 has a body 1201. Body 1201 contains or supports a drive system. The drive system includes a drive member 1207. The drive member 1207 may be a flexible shaft, for example.

Body 1201 is connected to a neck 1221 at a first end of neck 1221. A brush assembly is connected to a second end of neck 1221. Body 1201 may define an opening for access to the drive system. A first button, switch, or other now known or later developed actuating mechanism 1223 may be connected to the drive system and accessible through the opening of body 1201. A second button, switch, or other now known or later developed actuating mechanism 1225 may be connected to the drive system and accessible through the opening of body 1201. Actuating mechanism 1225 may be configured to enable and cause an adjustment of the drive system. For example, actuating mechanism 1225 may facilitate turning multi-functional electric brush 1200 on and off and adjusting a speed of the drive system. Drive member 1221 may be flexible to accommodate angled extension from body 1201 to the brush assembly. In some embodiments, the angle may be about 20 degrees.

Figure 13:
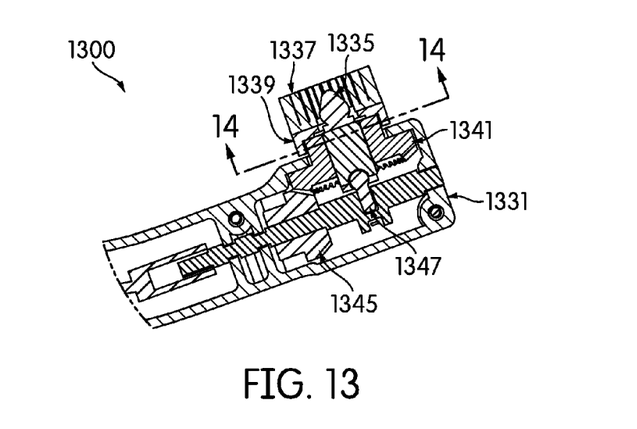
FIG. 13 is a exploded view of a brush assembly, according to an embodiment of the present invention.

FIG. 13 is an exploded view of a brush assembly 1300, according to an embodiment of the present invention. Brush assembly 1331 includes an interdental cleaning member 1335 and an outer brush member 1337. Outer brush member 1337 may be configured to form a ring defining a central opening, and interdental cleaning member 1335 may be disposed for movement inside the ring in a direction substantially perpendicular to a direction of rotation of outer brush member 1337.

Outer brush member 1337 may be supported by a brush support member 1339. The drive member may be contained or supported within a drive shaft defined by the neck. The drive member may be connected at a second end to a crankshaft assembly having a brush assembly support gear 1341 and a drive member gear 1345. Drive member gear 1345 may be attached to and rotated by the drive member. Drive member gear 1345 may be configured to interlock with and cause rotation of brush assembly support gear 1341.

The second end of the drive member may be attached to an offset connecting rod. The connecting rod may be associated with a ball and socket assembly 1347. The ball and socket assembly may connected to an interdental cleaning member 1335, and may be configured to cause the interdental cleaning member to move up and down in a direction perpendicular to direction of rotation of the drive member as the drive member rotates.

Brush support member 1339 may be connected to brush assembly gear 1341. When the drive member is rotated, drive member gear 1345 rotates brush assembly gear 1341, thus rotating outer brush 1337 attached to brush support 1339. Meanwhile, the rotating drive member moves the connecting rod and ball and socket assembly to cause pulsing movement of interdental cleaning member 1335 through the central opening of outer brush 1337. In some embodiments, interdental cleaning member 1335 may also be connected to brush assembly gear 1341 to enable rotation of cleaning member 1335 during the pulsing. For example, when a gear ratio of brush assembly gear 1341 and drive member gear 1345 is 1:2, the interdental brush may rotate at the same speed as outer brush 1337, and pulse in a direction perpendicular to a direction of rotation at a speed of about twice that of the speed of rotation of interdental brush 1335. Accordingly, such a multi-function brush advantageously enables simultaneous cleaning of flat tooth surfaces and interdental spaces.

Figure 14:
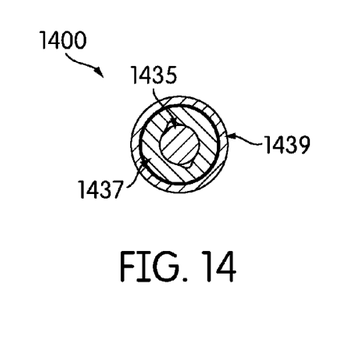
FIG. 14 is a top view of a brush assembly for a multi-functional electric brush according to an embodiment of the present invention.

FIG. 14 is a top view of a brush assembly 1400, according to an embodiment of the present invention. Brush assembly 1400 includes a centrally disposed interdental cleaning member 1435. Interdental cleaning member 1435 is configured to rotate and pulse within the opening defined by an outer brush 1437. Outer brush 1437 may be attached to and supported by a brush support 1439. Interdental cleaning member 1435 may be configured to meet support member 1439 to cause rotation of interdental cleaning member 1435 as support member 1439 rotates.

Figure 15:
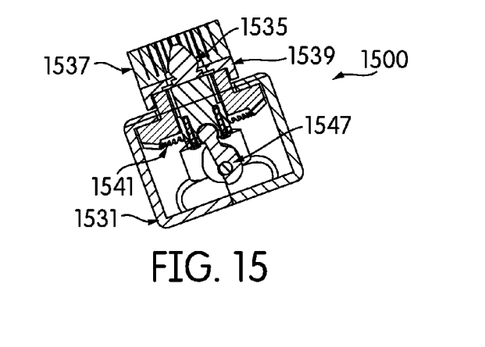
FIG. 15 is a cross-sectional end view of a head of a multi-functional electric brush, according to an embodiment of the present invention.

FIG. 15 is a cross-sectional end view of a head 1500 of a multi-functional electric brush, according to an embodiment of the present invention. Head 1500 includes an interdental cleaning member 1535 and an outer brush member 1537. Outer brush member 1537 may be configured to form a ring defining a central opening, and interdental cleaning member 1535 may be disposed for movement inside the ring in a direction substantially perpendicular to a direction of rotation of brush member 1537.

Outer brush member 1537 may be supported by a brush support member 1539. The drive member may be contained or supported within a drive shaft defined by the neck. The drive member may be connected at a second end to a crankshaft assembly having a brush assembly support gear 1541 and a drive member gear 1545. Drive member gear 1545 may be attached to and rotated by the drive member. Drive member gear 1545 may be configured to interlock with and cause rotation of brush assembly support gear 1541.

The second end of the drive member may be attached to an offset connecting rod. The connecting rod may be associated with a ball and socket assembly 1547. The ball and socket assembly may connected to an interdental cleaning member 1535, and may be configured to cause the interdental cleaning member to move up and down in a direction perpendicular to direction of rotation of the drive member as the drive member rotates.

Brush support member 1539 may be connected to brush assembly gear 1541. When the drive member is rotated, drive member gear 1545 rotates brush assembly gear 1541, thus rotating outer brush 1537 attached to brush support 1539. Meanwhile, the rotating drive member moves the connecting rod and ball and socket assembly to cause pulsing movement of interdental cleaning member 1535 through the central opening of outer brush 1537. In some embodiments, interdental cleaning member 1535 may also be connected to brush assembly gear 1541 to enable rotation of cleaning member 1535 during the pulsing. For example, when a gear ratio of brush assembly gear 1541 and drive member gear 1545 is 1:2, the interdental brush may rotate at a same speed as outer brush 1537, and pulse in a direction perpendicular to a direction of rotation at a speed of about twice that of the speed of rotation of interdental brush 1535. Accordingly, such a multi-function brush advantageously enables simultaneous cleaning of flat tooth surfaces and interdental spaces.

Figure 16A:
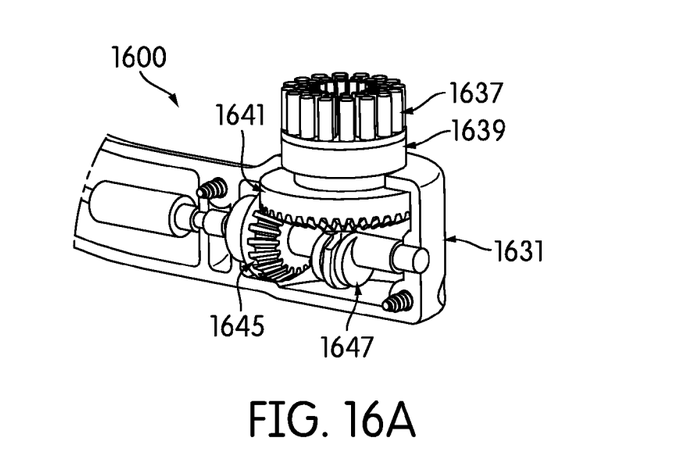
FIG. 16A is a perspective view of a head of a multi-functional electric brush, according to an embodiment of the present invention.
Figure 16B:
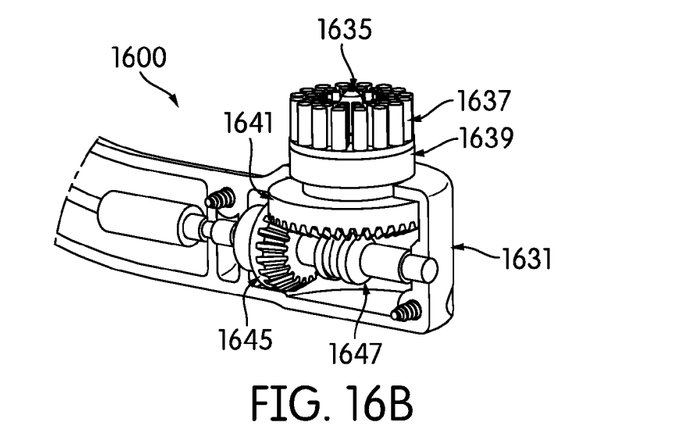
FIG. 16B is another perspective view of the head of the multi-functional electric brush, according to an embodiment of the present invention.
Figure 16C:
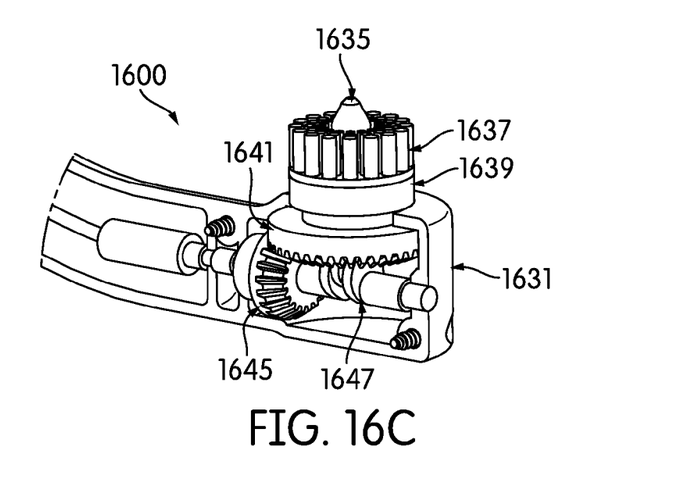
FIG. 16C is yet another perspective view of the head of the multi-functional electric brush, according to an embodiment of the present invention.

FIGS. 16A-C are perspective views of a head 1600 of a multi-functional electric brush with an interdental member in different positions, according to an embodiment of the present invention. Head 1600 includes an interdental cleaning member 1635 and an outer brush member 1637. Outer brush member 1637 may be configured to form a ring defining a central opening, and interdental cleaning member 1635 may be disposed for movement inside the ring in a direction substantially perpendicular to a direction of rotation of outer brush member 1637.

Outer brush member 1637 may be supported by a brush support member 1639. The drive member may be contained or supported within a drive shaft defined by the neck. The drive member may be connected at a second end to a crankshaft assembly having a brush assembly support gear 1641 and a drive member gear 1645. Drive member gear 1645 may be attached to and rotated by the drive member. Drive member gear 1645 may be configured to interlock with and cause rotation of brush assembly support gear 1641.

The second end of the drive member may be attached to an offset connecting rod. The connecting rod may be associated with a ball and socket assembly 1647. The ball and socket assembly may connected to interdental cleaning member 1635, and may be configured to cause interdental cleaning member 1635 to move up and down in a direction perpendicular to direction of rotation of the drive member as the drive member rotates. In FIG. 16A, interdental cleaning member 1635 is obscured by outer brush 1637. Interdental cleaning member 1635 is in a first position where ball and socket assembly 1647 supports interdental cleaning member 1635 in a position that is lower than a top operating surface of outer brush 1637. In FIG. 16B, interdental cleaning member 1635 is located at a second position that is about midway between the first non-extended position shown in FIG. 16A and a third position shown in FIG. 16C, where interdental cleaning member 1635 is substantially fully extended and is positioned beyond an operating surface of outer brush 1637.

Brush support member 1639 may be connected to a brush assembly gear 1641. When the drive member is rotated, the drive member gear is caused to rotate brush assembly gear 1641, thus rotating the outer brush 1637 attached to brush support 1639. Meanwhile, the rotating drive member moves the connecting rod and ball and socket assembly to cause pulsing movement of interdental cleaning member 1635 through the central opening of the outer brush 1637. In some embodiments, interdental cleaning member 1635 may also be connected to brush assembly gear 1641 to enable rotation of the cleaning member during the pulsing. For example, when a gear ratio of brush assembly gear 1641 and drive member gear 1645 is 1:2, interdental cleaning member 1635 may rotate at a same speed as outer brush 1637, and pulse in a direction perpendicular to a direction of rotation at a speed of about twice that of the speed of rotation of interdental cleaning member 1635. Accordingly, such a multi-function brush advantageously enables simultaneous cleaning of flat tooth surfaces and interdental spaces.

Accordingly, the multi-function brush in accordance with some embodiments advantageously enables simultaneous cleaning of flat tooth surfaces and interdental spaces. The combined operable surface area of the interdental cleaning member and the outer brush may enhance cleaning of tooth surfaces. For example, the combination of the interdental cleaning member and the outer brush may form a total operable surface area that is 50% larger than an operable surface area of the outer brush alone. Further, the multi-function brush in accordance with some embodiments may be useful for many applications, including pedodontal, and orthodontic applications.

The multi-function brush in accordance with some embodiments may be useful for periodontal applications, and may enable enhanced cleaning under the gumline. For example, the multi-function brush in accordance with some embodiments may include an interdental cleaning member that is configured to reach about 3 to 5 millimeters below the gumline for cleaning. The multifunction brush in accordance with some embodiments may enable cleaning at about 5 millimeters below the gumline. The interdental cleaning member and the outer brush may combine to form a top operable cleaning surface that enables enhanced cleaning functionality.

It will be readily understood that the components of various embodiments of the present invention, as generally described and illustrated in the figures herein, may be arranged and designed in a wide variety of different configurations. Thus, the detailed description of the embodiments of the systems, apparatus, and methods of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

The modifiers "about" and "approximately" used in connection with a quantity are inclusive of the stated value and have the meaning dictated by the context. For example, it includes at least the degree of error associated with the measurement of the particular quantity. When used with a specific value, they also disclose that value.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention.

In order to determine the metes and bounds of the invention, therefore, reference should be made to the appended claims.

What is claimed is:

1. A powered dental and interdental cleaning apparatus, comprising:
   a body comprising a first end and a second end;
   a head comprising a first brush assembly and a second brush assembly, the second brush assembly comprising an interdental cleaning member configured to clean interdental spaces, tooth surfaces, and periodontal surfaces;
   a flexible drive member extending from the first end of the body at an angle to a longitudinal axis of the body, the drive member connected to the interdental cleaning member and configured to cause the interdental cleaning member to pulse and rotate; and
   a neck comprising a first end and a second end, the neck extending from the first end of the body at the first end of the neck, and the neck defining a drive member shaft that contains the drive member.

2. The apparatus of claim 1, the drive member further comprising the drive member configured to cause the first brush assembly to rotate in a first direction, the drive member configured to cause the second brush assembly to pulse in a second direction, wherein the second direction is substantially perpendicular to the first direction.

3. The apparatus of claim 2, wherein the first brush assembly further comprises:
   a plurality of bristle tufts disposed to form a ring that surrounds the second brush assembly.

4. The apparatus of claim 3, wherein the second brush assembly further comprises:
   a central bristle tuft.

5. The apparatus of claim 4, wherein the first brush assembly further comprises:
   a first brush assembly support configured to support the plurality of bristle tufts.

6. The apparatus of claim 5, wherein the second brush assembly further comprises a second brush assembly support configured to support the central bristle tuft.

7. The apparatus of claim 1, wherein the drive member extends from the body at an angle of about 20 degrees.

8. The apparatus of claim 1, comprising:
   an offset connecting member; and
   a ball and socket assembly, the drive member being directly connected to the offset connecting member, the offset connecting member being connected to the ball and socket assembly.

9. The apparatus of claim 1, comprising:
   a brush support member supporting a brush of the first brush assembly and defining an opening; and
   an interdental cleaning member support, the interdental cleaning member support axially moveable from a first position to a second position, wherein the interdental cleaning member support is disposed below the opening in the first position and exposed above the opening in the second position.

10. The apparatus of claim 9, wherein the brush support member is rotatable.

11. The apparatus of claim 1, wherein the interdental cleaning member is configured to reach approximately 3 to 5 millimeters below the gumline, and preferably is configured for cleaning at about 5 millimeters below the gumline.

12. A brush assembly, comprising:
   an outer brush forming a ring that defines a central opening; and
   an interdental cleaning member configured to clean interdental spaces, tooth surfaces, and periodontal surfaces, the interdental cleaning member surrounded by the outer brush, wherein the outer brush and the interdental cleaning member are configured and arranged to enable the interdental cleaning member to reciprocate and rotate axially through the opening.

13. The apparatus of claim 12, further comprising:
   an outer brush support; and
   an interdental cleaning member support, the outer brush support being configured to contact the interdental cleaning member to cause the interdental cleaning member to rotate by the outer brush support.

14. The apparatus of claim 13, wherein the interdental cleaning member support is configured to move the interdental cleaning member in a first direction toward a position such that the interdental cleaning member extends 5 millimeters beyond an operable surface of the outer brush.

15. The apparatus of claim 14, wherein the outer brush support is configured to rotate the outer brush and the interdental cleaning member is configured to move in a direction that is substantially perpendicular to a direction of rotation of the outer brush.

16. The apparatus of claim 13, wherein the interdental cleaning member support is configured to move the interdental cleaning member in a first direction toward a position such that the interdental cleaning member extends beyond an operable surface of the outer brush.

17. The apparatus of claim 13, wherein the outer brush support is rotatable.

18. A powered dental and interdental cleaning apparatus, comprising:
   an outer brush forming a ring that defines a central opening;
   an interdental cleaning member surrounded by the outer brush, wherein the outer brush and the interdental cleaning member are configured and arranged to enable the interdental cleaning member to reciprocate axially through the opening member, the interdental cleaning member configured to clean interdental spaces, tooth surfaces, and periodontal surfaces;
   a drive assembly configured to rotate the outer brush and concurrently cause pulsing movement of the interdental cleaning member: and
   an electric motor, the motor powering the drive assembly.

19. The apparatus of claim 18, wherein the drive assembly further comprises:
   the drive member extending from a first end of a body at an angle to a longitudinal axis of the body, wherein the drive member is connected to the interdental cleaning member and the outer brush to rotate the outer brush and cause the interdental cleaning member to move axially.

20. The apparatus of claim 18, motor further comprising:
   a variable speed motor connected to and configured to drive the drive member, wherein the drive member extends from the body at an angle of about 20 degrees.

* * * * *